US008521457B2

(12) United States Patent
Patel et al.

(10) Patent No.: US 8,521,457 B2
(45) Date of Patent: Aug. 27, 2013

(54) USER DESIGNATED MEASUREMENT DISPLAY SYSTEM AND METHOD FOR NDT/NDI WITH HIGH RATE INPUT DATA

(75) Inventors: Jayesh Patel, Salisbury, MA (US); Michael Drummy, North Reading, MA (US)

(73) Assignee: Olympus NDT, Waltham, MA (US)

( * ) Notice: Subject to any disclaimer, the term of this patent is extended or adjusted under 35 U.S.C. 154(b) by 241 days.

(21) Appl. No.: 12/254,290

(22) Filed: Oct. 20, 2008

(65) Prior Publication Data

US 2010/0100344 A1    Apr. 22, 2010

(51) Int. Cl.
| | |
|---|---|
| *G01R 19/00* | (2006.01) |
| *G01N 11/00* | (2006.01) |
| *G01N 27/82* | (2006.01) |
| *G01N 29/06* | (2006.01) |
| *G01N 27/90* | (2006.01) |

(52) U.S. Cl.
CPC ............... *G01N 27/82* (2013.01); *G01N 27/90* (2013.01); *G01N 29/0618* (2013.01)
USPC ................... 702/64; 702/56; 702/54; 702/59; 702/67; 702/171

(58) Field of Classification Search
CPC ......................... G01N 29/0618; G01N 29/0645
USPC .................................................. 702/38, 64
See application file for complete search history.

(56) References Cited

U.S. PATENT DOCUMENTS

| | | | | |
|---|---|---|---|---|
| 3,688,565 A | * | 9/1972 | Brech | ............................. 73/628 |
| 3,955,405 A | * | 5/1976 | Couture | ........................ 73/609 |
| 4,333,345 A | * | 6/1982 | Renzel et al. | ................... 73/606 |
| 4,695,833 A | * | 9/1987 | Ogura et al. | ............... 345/440.1 |
| 5,063,515 A | * | 11/1991 | Kunst et al. | .................... 701/99 |
| 5,250,935 A | * | 10/1993 | Jonker et al. | ............... 345/440.1 |
| 5,255,365 A | * | 10/1993 | Hungerbuhler | ............ 345/440.1 |
| 5,285,521 A | * | 2/1994 | Holt et al. | ...................... 704/270 |
| 5,375,067 A | * | 12/1994 | Berchin | ......................... 702/66 |
| 5,661,658 A | * | 8/1997 | Putt et al. | ........................ 702/68 |
| 5,706,204 A | * | 1/1998 | Cox et al. | ........................ 702/67 |
| 6,311,138 B2 | * | 10/2001 | Miller | ............................. 702/67 |
| 6,344,844 B1 | * | 2/2002 | Timm et al. | ................ 345/440.1 |
| 6,522,345 B1 | * | 2/2003 | Alexander | .................... 715/771 |
| 6,615,148 B2 | * | 9/2003 | Pickerd | ........................... 702/66 |
| 6,731,286 B2 | * | 5/2004 | Ritter | ............................ 345/440 |
| 6,862,022 B2 | * | 3/2005 | Slupe | ............................ 345/207 |
| 7,031,778 B2 | * | 4/2006 | Hsiung et al. | ................... 700/29 |
| 7,184,922 B2 | * | 2/2007 | Ousley et al. | ................. 702/127 |
| 7,577,533 B2 | * | 8/2009 | Buschke et al. | ............... 702/39 |
| 7,877,233 B2 | * | 1/2011 | Middleton et al. | ............ 702/187 |

(Continued)

FOREIGN PATENT DOCUMENTS

DE            3700368 C1 *  6/1988

*Primary Examiner* — Jonathan Teixeira Moffat
*Assistant Examiner* — Timothy H Hwang
(74) *Attorney, Agent, or Firm* — Ostrolenk Faber LLP

(57) ABSTRACT

A user configured measurement display system and method for a non-destructive testing device and instrument (NDT/NDI) with high input data rate is disclosed. The system and the method provide the means for NDT/NDI instruments display measurement values that satisfies user designated measurement criterion occurring during any measurement time intervals (MTIs). The present disclosure overcomes the shortcomings of conventional ways of picking and displaying measurement values at fixed MTIs, by which the values truly satisfying the measurement criterion that occurs at random MTIs (other than scheduled MTIs) are often skipped.

21 Claims, 8 Drawing Sheets

(56) References Cited

U.S. PATENT DOCUMENTS

2002/0067359 A1* 6/2002 Brodsky et al. ............... 345/440
2005/0015209 A1* 1/2005 Wuebker ........................ 702/38
2007/0084290 A1* 4/2007 Fetzer et al. .................... 73/627
2007/0213956 A1* 9/2007 Nasle et al. ................... 702/182

* cited by examiner

USER DESIGNATED MEASUREMENT DISPLAY SYSTEM AND METHOD FOR NDT/NDI WITH HIGH RATE INPUT DATA

FIELD OF THE DISCLOSURE

The present disclosure generally relates to an electronic measurement display system and method, more particularly, to a user designated measurement display system and method for non-destructive testing, or inspection (NDT/NDI), using an instrument operating at a high measurement rate.

BACKGROUND OF THE DISCLOSURE

Industrial non-destructive testing instruments are used for various types of applications, such as material flaw detection, corrosion monitoring and thickness measurement. The prior art for such devices typically energizes, acquires and processes sensor signals, and issues resulting alarm signals at a substantially faster rate than the rate at which the data associated with said signals are provided to the display for image update. User observation and interpretation of display images are important aspects of the inspection process; therefore, it can pose a problem when the instrument operator cannot be assured that the displayed image is substantially coincident with the alarm event.

It is important to note that it is not uncommon for NDT/NDI instruments to have a display image update at 60 Hz, a rate at which the differences of consecutive image updates can not be discerned by the human eye. The benefit of the instrument operator being assured that the displayed image is substantially coincident with the alarm event is realized when an indication that an alarm event has occurred is shown on the display, and afterwards the operator carefully positions the sensor at a location on the object under inspection that produces a persistent alarm indication. When the position is located, the display image will represent the alarm condition for consecutive 60 Hz updates, thereby allowing the operator to clearly see the persisting alarm event. Typically, the fields of each display image will be comprised of a waveform, waveform markers, numeric readings, and an alarm occurrence indicator. Any one, or a combination, of fields will blink, or otherwise distinctly change, when a persistent alarm condition begins to occur. Furthermore, the display image field update rate of distinctive changes may in some embodiments change at a rate proportional to the number of alarm events per fixed period of time in order to let the operator know the quality of the current inspection measurement. One of the distinctive changes may be changing to a persistent, non-blinking, indication meaning that the highest degree of persistent alarm events is occurring.

One way to address the display/alarm coincidence problem described above is to reduce the measurement and alarm update rate to be less than or equal to the display image update rate; however, this can only be done at the expense of the real time measurement performance of the inspection process. A high frequency measurement rate, as compared to the display image update rate, provides the advantage of higher efficiency because a sensor can be moved at a higher speed along the surface of the object being inspected, or be moved at the regular, or slower, speed with a higher probability of detecting an alarm condition. In the example of a surface scanned at a rate of 10 cm per second, the sensor would traverse 0.167 cm for each 60 Hz measurement rate; however, if the measurement rate was 300 Hz, the sensor would traverse only 0.033 cm for each measurement rate time interval (MTI)—hence, the 300 Hz MTI provides a five fold improvement on scanning resolution. This is why it is not uncommon for NDT/NDI instruments to allow scans to be carried out with a measurement rate in a range of 300~10,000 Hz.

Alternatively, one could consider increasing the display image update rate to match the measurement rate; however, this is impractical because it places an onerous and unnecessary burden on the instrument's video processing system due to the increased bandwidth requirements and consequential power increase, and many otherwise suitable display technologies are incapable of such a high image update rate.

As a result, which measurement results can be displayed, what characteristics of the measurement may be selected to display, what results are skipped and how results are used in deducing the display result have become an engineering challenge for some to work on. More importantly, how to display an alarm event at a display rate for a real-time alarm event that occurs at the measurement rate has been a challenge to many in the field.

The deficiency of the prior art is obvious in that it does not discriminate between discrete MTI's when it involves providing display image update information; therefore, the instrument operator cannot be assured that the displayed image is substantially coincident with the alarm event. Consequently, any one of the five MTI's is used to update the display image at a 60 Hz rate without any deliberate correlation with the measurement event that caused an alarm.

SUMMARY OF THE DISCLOSURE

Accordingly, a general object of the present disclosure is to provide a user designated measurement display system and method for an ultrasonic detection device that uses high rate data acquisition.

Another object of the present disclosure is to provide a means for an operator or a user to designate measurement criterion or measurement event to be selected for display.

Yet another important object of the present disclosure is to make sure to display the true measured value of a designated criterion that could happen within any measurement time interval, without skipping measurement results which often happens when the display event is arbitrarily picked from a fixed number of measurement intervals.

The foregoing and other objects of the invention are realized with the circuit and system described more fully in the detailed description section and the drawings.

The foregoing and other objects, advantages and features of the present invention will become more apparent upon reading of the following non restrictive description of illustrative embodiments, given for the purpose of illustration only with reference to the appended drawings.

BRIEF DESCRIPTION OF THE DRAWINGS

FIG. 1 is a high level block diagram showing a typical instrument that the present disclosure is used for.

DETAILED DESCRIPTION OF PREFERRED EMBODIMENTS OF THE PRESENT DISCLOSURE

Although an ultrasonic sensor signal is described in the exemplary embodiment, it is not limited in this regard.

Figure 2:
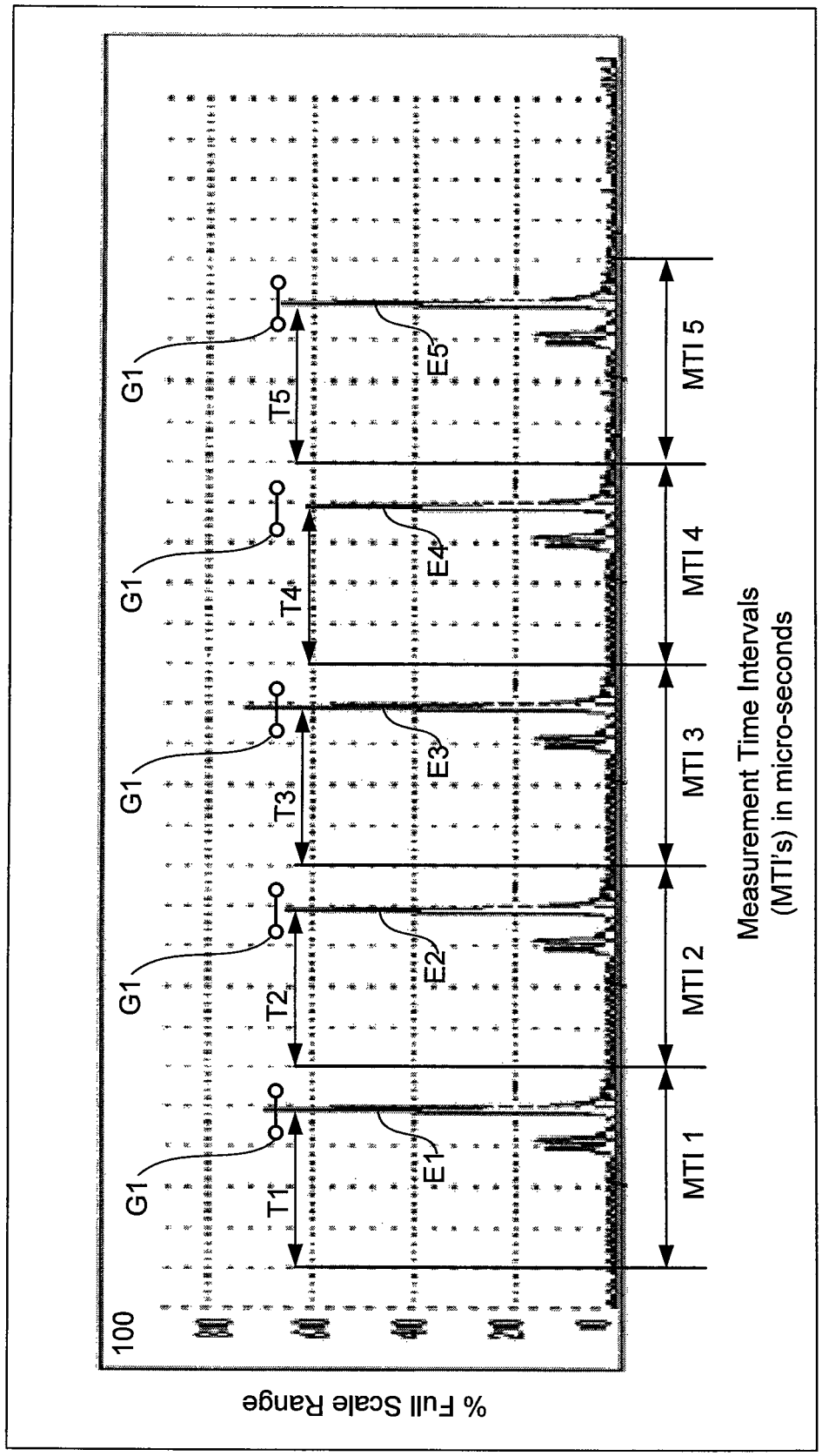
FIG. 2 shows five exemplary continuous measurement time intervals (MTI's) with echo signals and relevant associated parameters.

The preferred embodiment of the present disclosure ameliorates the aforementioned disadvantages of the prior art by ensuring that the information associated with MTI, or MTI's, that causes an alarm event to occur is also provided to the display at substantially the same time. The information associated with the MTI that causes an alarm event may be user defined by means of keypad 105 or remotely through a communications interface (not shown). Examples of how measurement results shown in FIG. 2 are signaled and displayed according to user defined alarm criteria are shown in Table 1 below. The parameters of Table 1 apply to FIG. 2.

TABLE 1

Alarm Event to be Signaled and Displayed by User Defined Criterion

| MTI | Measured Time Interval | Measured Amplitude (% of full scale range) | Alarm Criteria to trip gate (when gate G1 is set to 67% of Full Scale Range) | | | | |
|---|---|---|---|---|---|---|---|
| | | | 1) First echo amplitude | 2) Max amplitude echo | 3) Min amplitude echo | 4) Min time interval | 5) Max time interval |
| 1 | t1 = 10 usec | 69% | X | | | | X |
| 2 | t2 = 11 usec | 64% | | | | | |
| 3 | t3 = 9 usec | 74% | | X | | X | |
| 4 | t4 = 10.5 usec | 61% | | | | | |
| 5 | t5 = 9.5 usec | 67% | | | X | | |

Indeed, the advantages described in the present disclosure may be applied effectively to many other types of sensor technologies.

Figure 1:
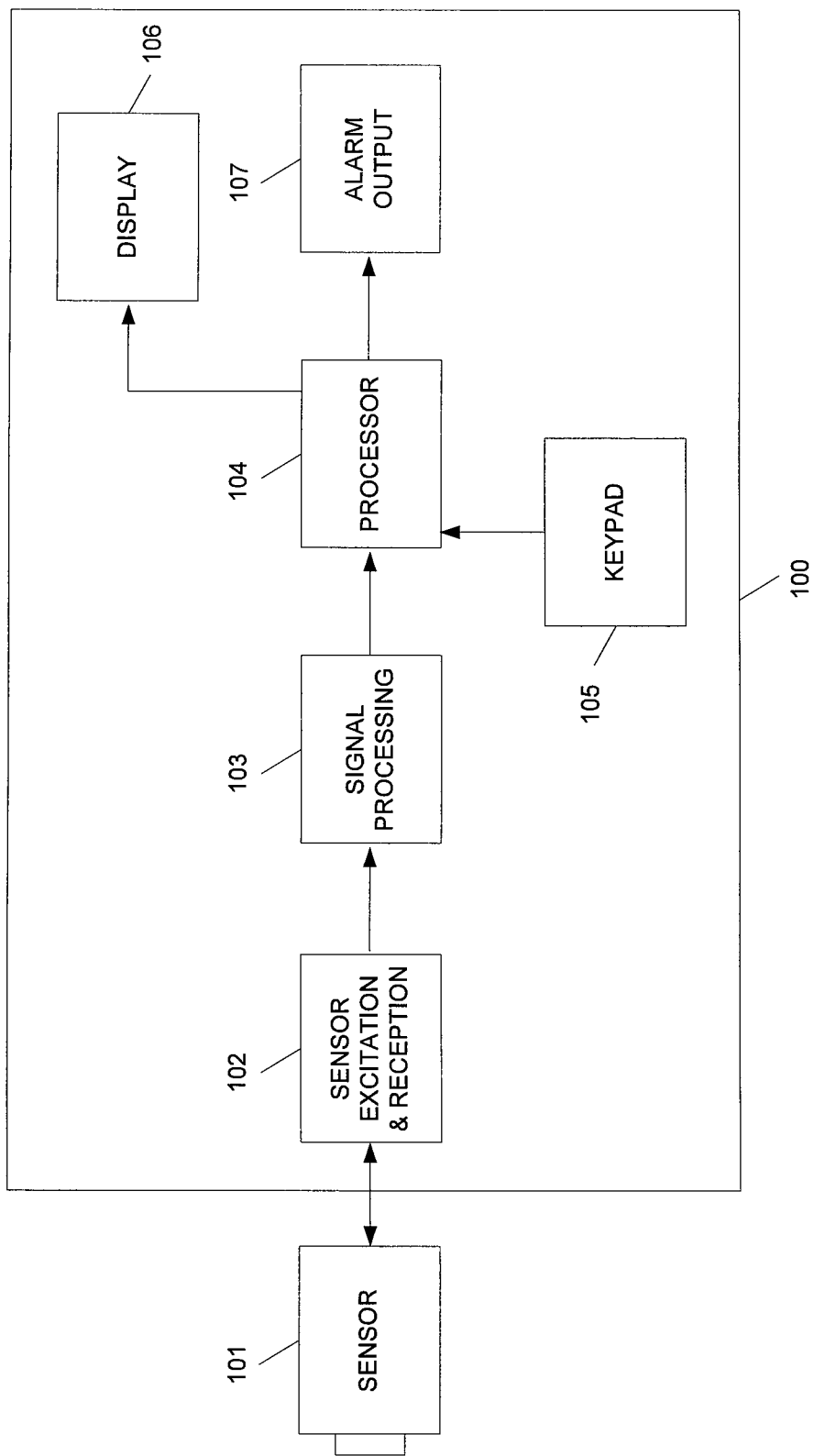

Referring to FIG. 1, a NDT/NDI instrument 100 is configured, controlled, and monitored by means of the user interface which is comprised of Display 106 and Keypad 105

Processor 104 is comprised of a microprocessor, memory, embedded program software, and other necessary support circuitry. It is responsible for overall control of NDT/NDI instrument 100. Signal Processing 103 processes signal provided by Sensor Excitation & Reception 102 connected to Sensor 101. Signal processing includes, but is not limited to, analog-to-digital conversion and filtering.

Sensor excitation & reception 102 provides drive signal to Sensor 101, the reflected information from which is provided to an amplifier stage (not shown), the output from which is provided to Signal Processing 103.

Display 106 is comprised of a screen that the measurement/waveform and information related to alarm events are displayed are at the display update rate. The display of information related to the alarm events is further described hereinafter.

Alarm Output 107 is updated at a measurement rate based on user selected alarm criterion. For clarification, this Alarm Output 107 is different than the Alarm Indicator 310 described hereinafter. Alarm Output 107 usually connects to a remote device, whereas the Alarm Indication 310 is a part of the screen of the Display 106.

As shown in FIG. 2, with the prior art method of display, measurement done in every five measurement time intervals (MTIs), for example, the $1^{st}$, $6^{th}$, $11^{th}$ and so on are displayed on the screen. (Measurements in MTIs $6^{th}$ and beyond are not shown and the description thereof is self explanatory). Four measurements between consecutive display updates, i.e. the $2^{nd}$, $3^{rd}$, $4^{th}$ and $5^{th}$ measurements and consecutively, the $7^{th}$, $8^{th}$, $9^{th}$ and $10^{th}$ measurements and so on, are not reported to display. If the alarm condition happens in those skipped measurements, the user will not see the corresponding measurement on the display.

Before discussing Table 1 further, it is worth noting that FIG. 2 is comprised of five MTI's, each of which includes response echo $E_n$, gate G1, and measured time interval $T_n$, where n indicates which MTI (1 through 5) E and T are associated with. The parameters for gate G1 are the same for all 5 MTI's. Although the present disclosure refers to $T_n$ in units of time, it is well understood by those skilled in the art that in an actual measurement applications time is expressed as thickness (e.g. inches or millimeters) because the primary interest when inspecting object under test 308 is either its thickness or location of a flaw within it. Converting time measurements accurately to thickness is possible because inspected objects are typically made of engineered materials having known and substantially constant sound velocity.

Typically, each MTI starts with an ultrasonic signal event, such as a transducer excitation pulse or an echo (both not shown in FIG. 2). The event represents the reference point from which time interval $T_n$ is measured and gate G1 is placed on the horizontal axis.

Figure 3:
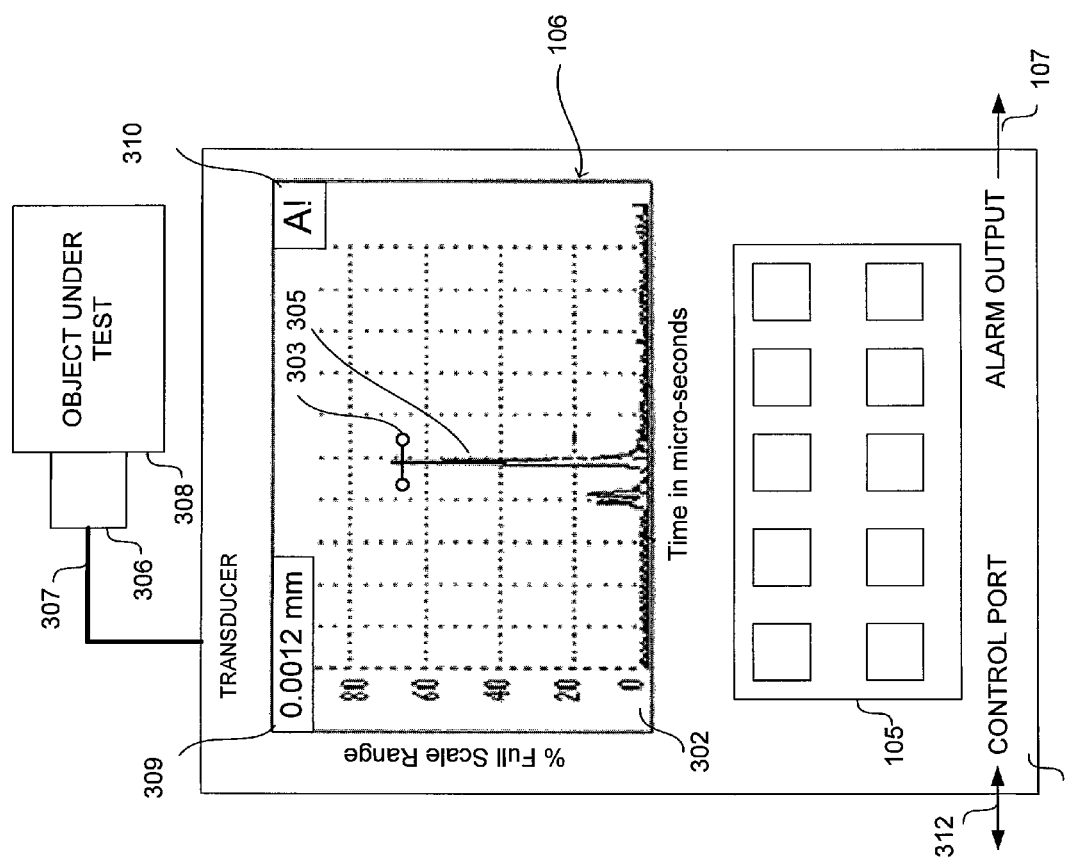
FIG. 3 shows an exemplary instrument with a display image that has been produced using one or more of the five contiguous MTI's.

Table 1 now is referred to in conjunction with FIGS. 1, 2 and 3 to describe an exemplary preferred embodiment of the present disclosure, wherein the MTI that causes the alarm event will be provided to the display on the next 60 Hz update. Regardless of which of the five Alarm Criteria is selected by the instrument user, the echo amplitude must meet or exceed a predetermined level set for gate G1 set by the user. The level is expressed as 'percent of full scale input range of the sampling system', and in the case of the present example is 67%.

Referring to FIG. 3, both the exemplary embodiment and prior art use an instrument, such as instrument 300, with transducer 306 to inspect object 308. Important aspects of the real time measurement process performed within the instruments are shown in FIG. 2. Instrument 300 operates with a display update rate of 60 Hz and a sensor measurement rate of 300 Hz as shown in FIG. 2. The display update rate is the rate at which new measurement information is provided to the display image. The sensor measurement rate is the rate at which the data acquisition and signal processing systems of instrument 300 produce new measurement information. The time period associated with the 300 Hz measurement rate is 3.33 ms, and is referred to as the measurement time interval (MTI). Echo 305 is one of the five echoes (i.e. E1 through E5 of FIG. 2) that will be provided to the display for each display update period. Gate G1 has the same parameters for both FIGS. 2 and 3.

Referring to FIG. 3, display 106 further comprises a Waveform Display area 302, Reading 309 and an Alarm indicator 310. Measurement and waveform information is updated and displayed in the Waveform Display area 302 at the display rate regardless of whether an alarm event has occurred. Reading 309 is the numeric measurement associated with the MTI concurrently displayed at 302, and ALARM INDICATOR 310 notifies the instrument operator that an alarm event has occurred.

Figure 4:
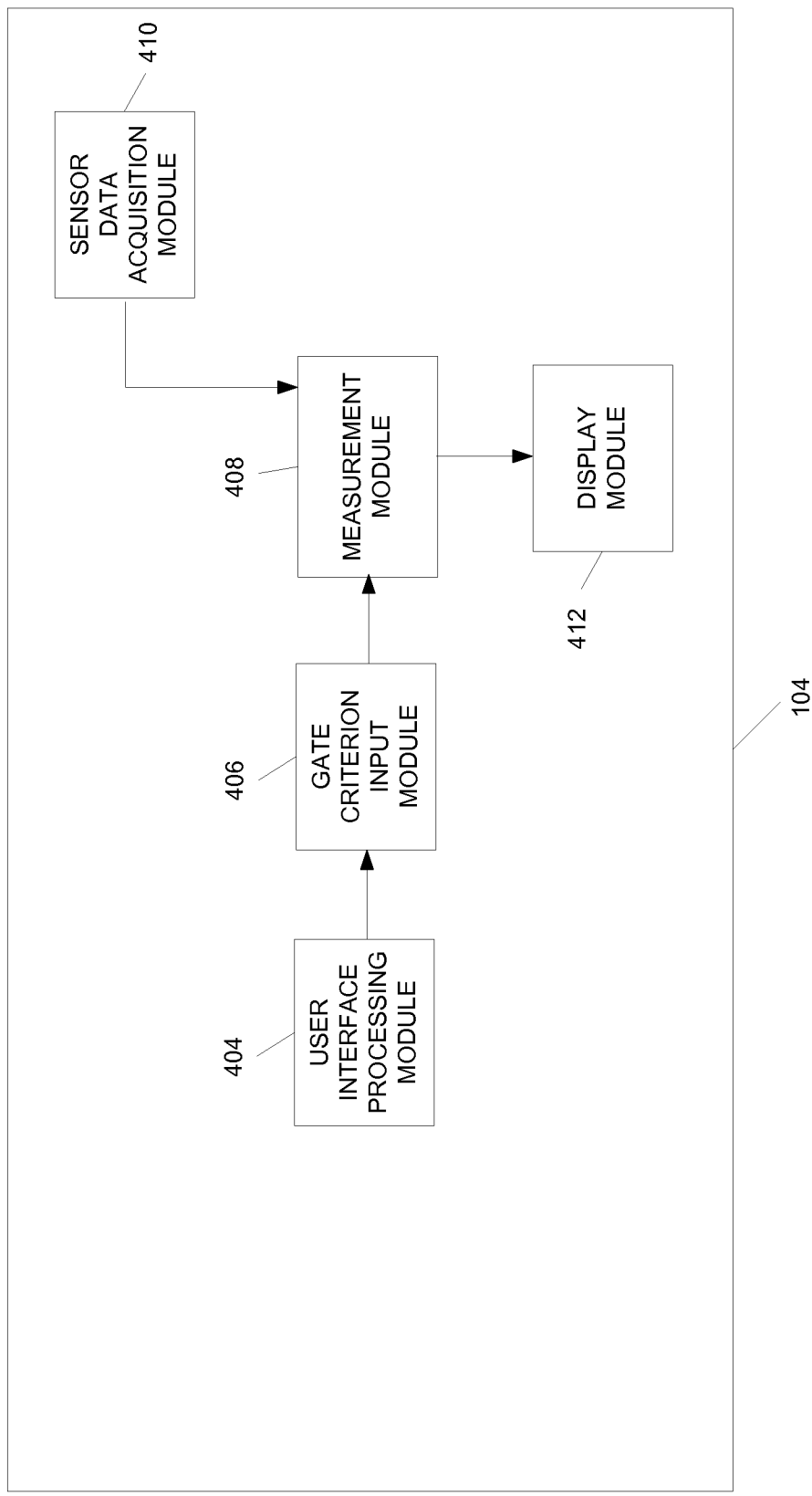
FIG. 4 is a block diagram for the software modules used to implement the present disclosure.

FIG. 4 shows the functional modules of a computer program residing in Processor 104 of FIG. 1. As shown in FIG. 4, processor 104 hosts a number of executable modules including a user interface processing module 404, a gate criterion input module 406, a measurement module 408, a sensor data acquisition module 410 and a display module 412. The measurement criterion is keyed in via Keypad 105 and processed by User Interface Processing Module 404 and Gate Criterion Input Module 406, then output data to Measurement Module 408. Echo Data Acquisition Module 410 input processed digital measurement data out to Measurement Module 408. Measurement Module 408 performs the following tasks:

1) Processes the data input from both Echo Data Acquisition Module and the Gate Criterion Module;
2) Computes and outputs Waveform display to Waveform Display 302 as shown in FIG. 3. based on the processing of contiguous MTI's occurring between each display image update; and
3) Executes a computer program that is described in a later part of this disclosure in FIGS. 5a-5c, to determine when to signal an alarm event according to the input from Echo Data Acquisition Module 410 and the data from the Gate Criterion Input Module 406.

Display Module 412 computes and forms graphic waveform to Waveform Display 302 at the measurement rate, and displays numerical display at Reading 309 and outputs an Alarm to Alarm Indicator 310.

Figure 5A:
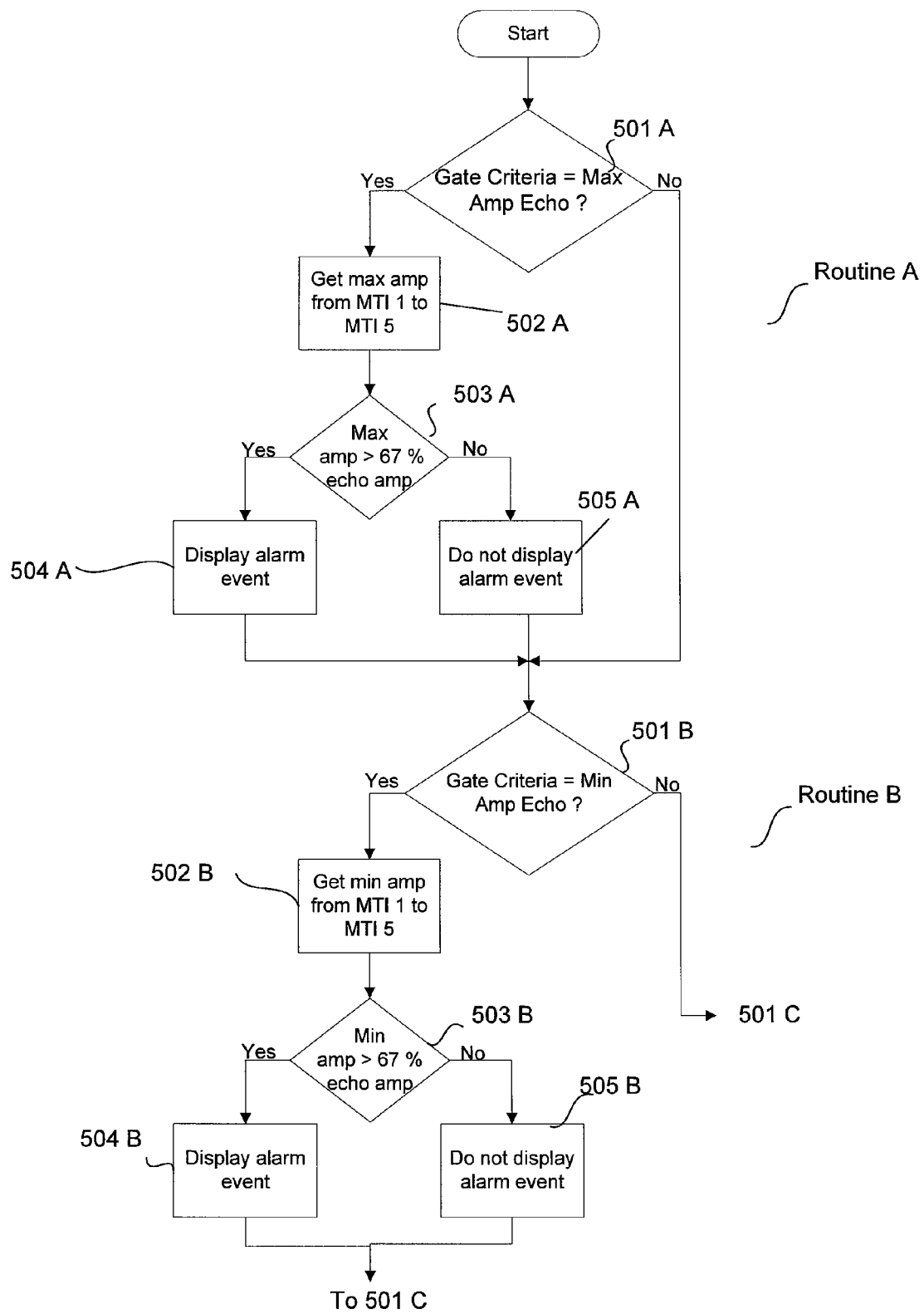
FIG. 5a shows a flow chart of part of the computer program executing the user designated event display.
Figure 5B:
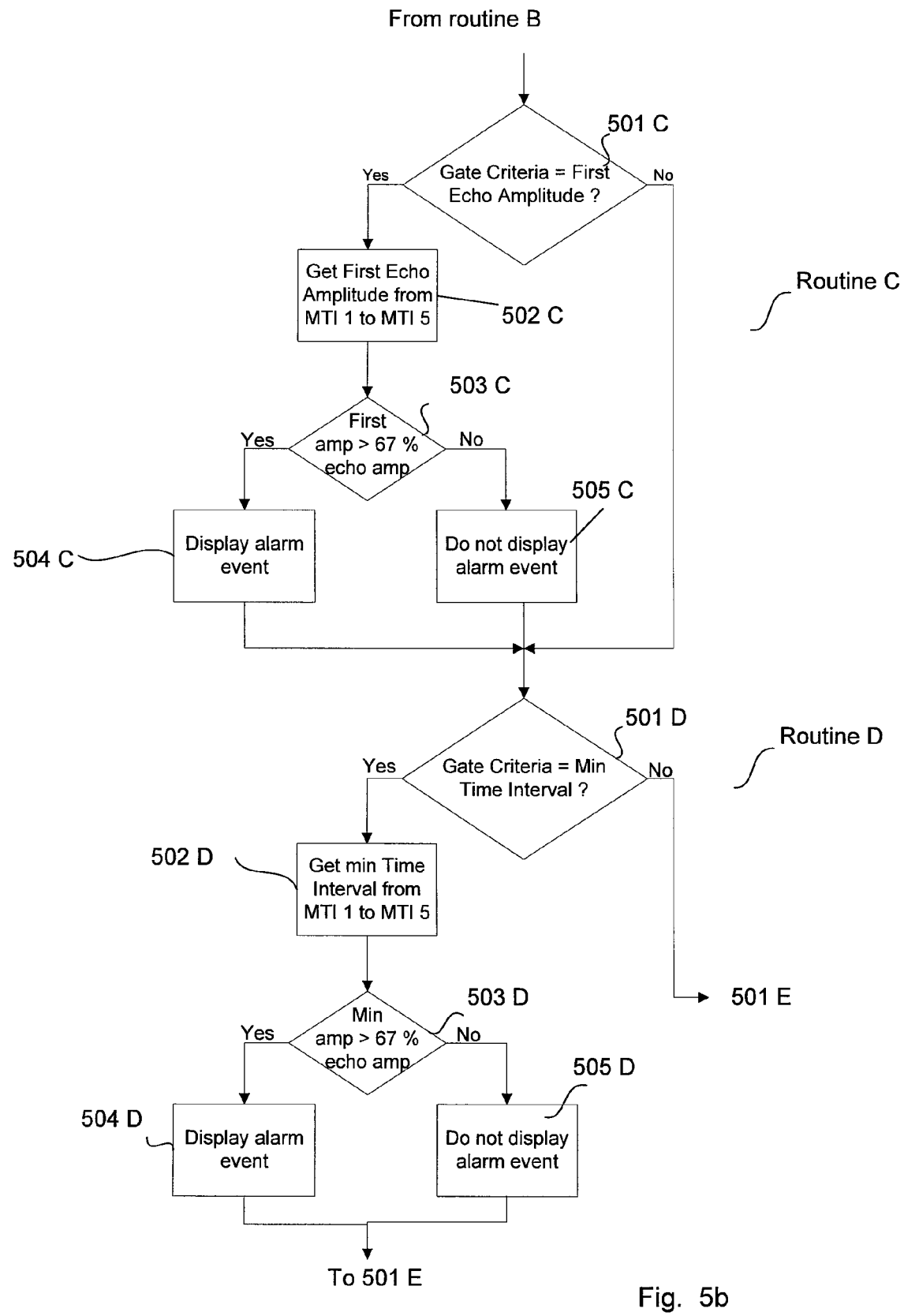
FIG. 5b shows a flow chart of another part of the computer program executing the user designated event display.
Figure 5C:
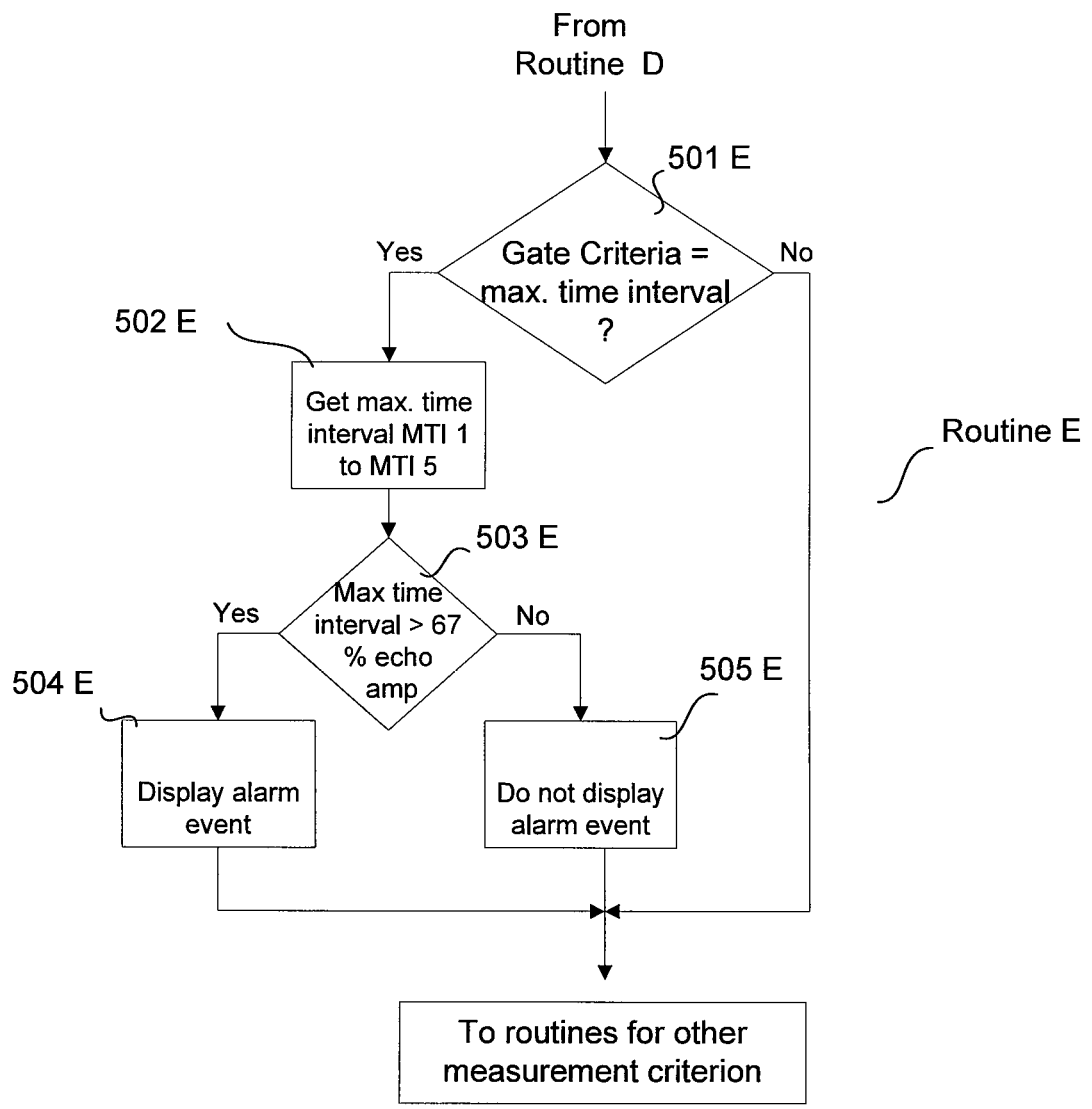
FIG. 5c shows a flow chart of yet another part of the computer program executing the user designated event display.

Referring to a computer program flow chart shown in FIG. 5, a preferred embodiment of Measurement Module 408 and Display Module 412 host a computing program that instructs processor 104 in FIG. 1 to execute the following steps of processes to perform the measurement display designed in this present disclosure. Although not shown in FIGS. 5a-5c, any time an alarm event is displayed, an alarm signal is provided to Alarm Output 107 (FIG. 3) within the same display update period.

Accordingly, the alarm events of Table 1 are carried out by the computer software as follows:

Step 501 A. Get gate criterion and check if the gate criterion is set to 'Maximum Echo amplitude'. If yes, then go to step 502 A. If no, go to step 501B.
Step 502 A. Get the highest echo amplitude from MTI 1 to MTI 5
Step 503 A. Check if the highest echo amplitudes between MTI 1 and MTI 5 meet the 67% echo amplitude criteria. If yes, go to Step 504 A. If not, go to Step 505 A.
Step 504 A. Display an alarm event at Alarm Indicator 310. At Reading 309, display the numerical value of the measurement for the parameter that caused the alarm event. Then go to Routine B.
Step 505 A. Do not display the alarm event. Then go to Routine B.
Step 501 B. Get gate criterion and check if the gate criterion is set to 'Minimum Echo amplitude'. If yes, then go to step 502 B. If no, go to step 501 C.
Step 502 B. Get the lowest echo amplitude from MTI 1 to MTI 5
Step 503 B. Check if the lowest echo amplitudes between MTI 1 and MTI 5 meet the 67% echo amplitude criteria. If yes, go to Step 504 B. If not, go to Step 505 B.
Step 504 B. Display an alarm event at Alarm Indicator 310. At Reading 309, display the numerical value of the measurement for the parameter that caused the alarm event. Then go to Routine C.
Step 505 B. Do not display the alarm event. Then go to Routine C.
Step 501 C. Get gate criterion and check if the gate criterion is set to 'First echo amplitude'. If yes, then go to step 502 C. If no, go to step 501 D.
Step 502 C. Get the first echo amplitude from MTI 1 to MTI 5
Step 503 C. Check if the first echo amplitudes between MTI 1 and MTI 5 meet the 67% echo amplitude criteria. If yes, go to Step 504 C. If not, go to Step 505 C.
Step 504 C. Display an alarm event at Alarm Indicator 310. At Reading 309, display the numerical value of the measurement for the parameter that caused the alarm event. Then go to Routine D.
Step 505 C. Do not display the alarm event. Then go to Routine D.
Step 501 D. Get gate criterion and check if the gate criterion is set to 'Minimum time interval'. If yes, then go to step 502 D. If no, go to step 501 E.
Step 502 D. Get Minimum time intervals from MTI 1 to MTI 5
Step 503 D. Check if Minimum time intervals between MTI 1 and MTI 5 meet the 67% echo amplitude criteria. If yes, go to Step 504 D. If not, go to Step 505 D.
Step 504 D. Display an alarm event at Alarm Indicator 310. At Reading 309, display the numerical value of the measurement for the parameter that caused the alarm event. Then go to Routine E.
Step 505 D. Do not display the alarm event. Then go to Routine E.
Step 501 E. Get gate criterion and check if the gate criterion is set to 'Maximum time interval'. If yes, then go to step 502 E. If no, go to step 506 E.
Step 502 E. Get the highest time intervals from MTI 1 to MTI 5
Step 503 E. Check if the maximum time intervals between MTI 1 and MTI 5 meet the 67% echo amplitude criteria. If yes, go to Step 504 E. If not, go to Step 505 E.
Step 504 E. Display an alarm event at Alarm Indicator 310. At Reading 309, display the numerical value of the measurement for the parameter that caused the alarm event. Then go to 501F.
Step 505 E. Do not display the alarm event. Then go to 501 F.
Step 501 F. Repeat the above steps for $MTI_6$, $MTI_7$, $MTI_8$, $MTI_9$, and $MTI_{10}$, and subsequently for all the rest of five consecutive time intervals until the end of the scan or measurement, and for any additional measurement criterion defined by the user.

Alternate Embodiment 1

A first alternate embodiment requires that more than one Alarm Criteria be applied to MTI's 1 through 5 in order to cause an alarm event. For example, Alarm Criteria 2 and 5 may be combined, requiring both to be met within a display update period in order to cause an alarm event, as would occur with MTI 3 and MTI 1 of table 1.

Alternate Embodiment 2

A second alternate embodiment requires no gate at all, and instead relies on a peak detect method of the echoes that occur within each MTI.

Alternate Embodiment 3

The problems associated with operator observation of important alarm events occurring at too fast of a display image update rate can also be remedied by use of the method described for the following alternate embodiment.

The method involves the indexing of alarm events by determining the sensor's position and storing into memory the position coordinates and other items of information associated with the type of alarm selected for storage. It should be noted that either a single, dual, or triple axis linear position encoder device may be used to provide the location coordinates of the instrument sensor.

In addition to routines A through D in FIGS. 5a, 5b and 5c, the alternate embodiment of Measurement Module 408 and Display Module 412 hosts a computing program that instructs Processor 104 in FIG. 1 to execute a routine to allow the alarm events to be indexed and stored for later review after the measurement.

Figure 6:
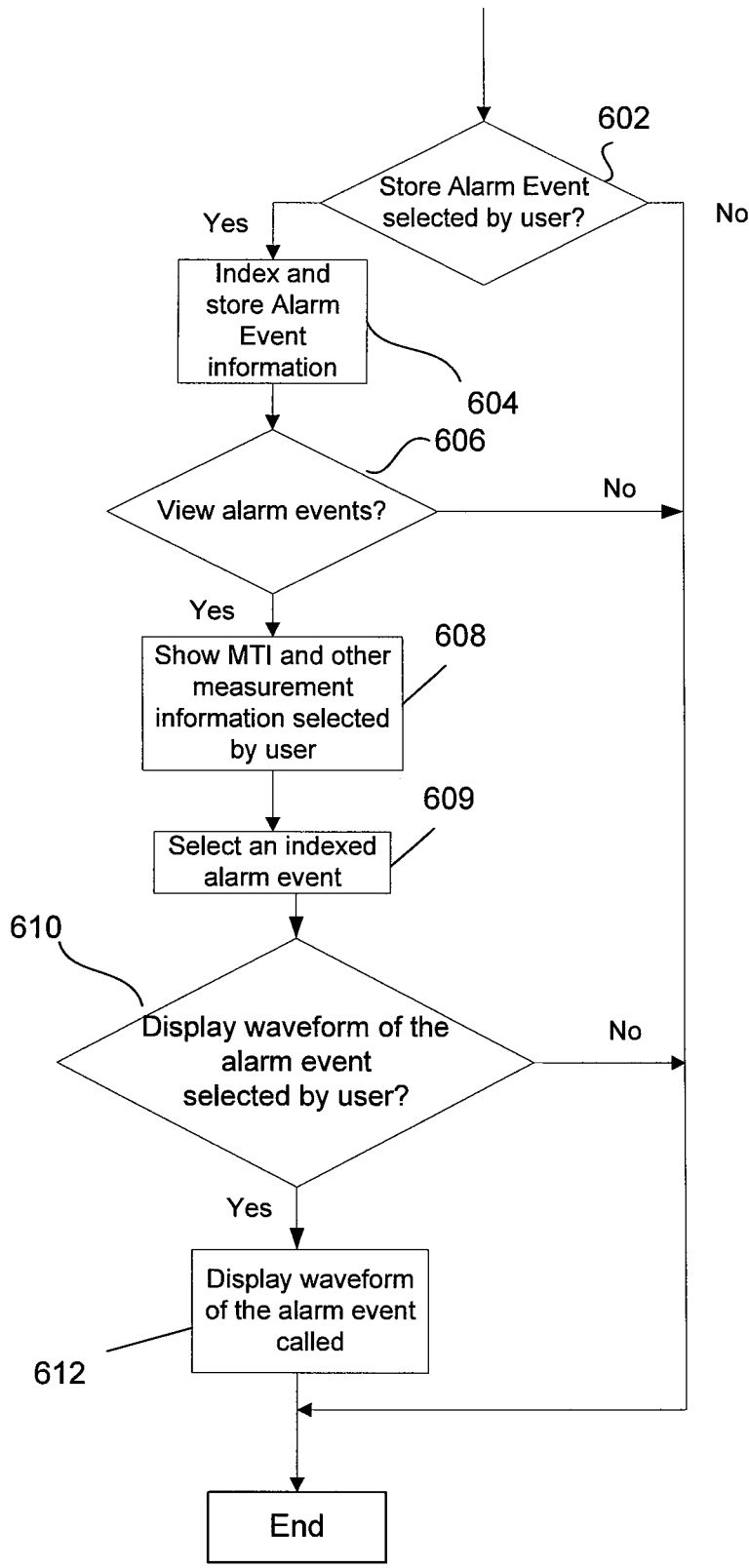
FIG. 6 shows a flow chart of the computer program executing the program associated with alternate embodiment 3.

Referring to FIG. 6, before any measurement begins, the user selects and stores via Keypad 105, or Control Port 312, (i.e., the user interface), which, if any, alarm event type and associated information will be stored. At Step 602, the program queries the storage location to determine the user's selection. If any alarm event type is selected to be stored and retrieved for later viewing, alarm events will be indexed and stored into Processor 104. Time, MTI, Alarm Criteria, and waveform are examples of information that may be stored in memory for a specific alarm event. The alternate embodiment provides the means for the user to select whether the waveform associated with each event should be stored. It should be obvious to those skilled in the art that embodiments can be realized that allow the user to select any combination of information to be stored or viewed later.

Continuing with FIG. 6, at Step 606, the program queries the memory location where the status of the user's selection is stored to determine whether the user wants to view the indexed alarm event information. If the status indicates that alarm events will be viewed, Step 608 will provide the indexed information for viewing, except for the measurement waveform. If the status indicate that the user does not want to view indexed alarm events, the program ends.

At Step 609, the program queries the memory location where the status of the user's selection is stored to determine whether the user wants to view the waveform associated with the indexed alarm event selected. If the status is affirmative, Step 610 displays the waveform for review; otherwise, the program ends.

Alternate Embodiment 4

As mentioned earlier in the background section of the present disclosure, but now with specific reference to FIG. 3, it is not uncommon for NDT/NDI instruments to have a display image 302 update at 60 Hz, a rate at which the differences of consecutive image updates can not be discerned by the human eye. The benefit of the instrument operator being assured that the display image 302 is substantially coincident with the alarm event is realized when an indication that an alarm event has occurred is shown on the display, and afterwards the operator carefully positions sensor 306 at a location on object under inspection 308 that produces a persistent alarm indication by means of field 310, for example. When the position is located, display image 302 will represent the alarm condition for consecutive 60 Hz updates, thereby allowing the operator to clearly see the persisting alarm event. Typically, the fields of each display image will be comprised of waveform 305, waveform marker 303, numeric readings 309, and an alarm occurrence indicator 310. Any one, or a combination, of fields will blink, or otherwise distinctly change, when a persistent alarm condition begins to occur. Furthermore, the display image field update rate of distinctive changes may in some embodiments change at a rate proportional to the number of alarm events per fixed period of time in order to let the operator know the quality of the current inspection measurement. One of the distinctive changes may be changing to a persistent, non-blinking, indication meaning that the highest degree of persistent alarm events is occurring.

Therefore, as described above, the present disclosure provides a user designated measurement display system and method for an ultrasonic detection device with high acquisition data rate comprising a sensor data acquisition module, a criterion input module, a user interface processing module, a measurement module and a display processing module. The system and method further comprises a means to display measurement values occurring during any measurement time interval that satisfies user designated measurement criterion.

What is claimed is:

1. A non-destructive detection device including a measurement and display system, comprising:
   a sensor facility configured to acquire measurement data for a test object during a continuous test time period, at an acquisition data rate associated with a plurality of measurement time intervals (MTI) for each acquisition session;
   a user display configured to display measurement results as alarm events at a display rate substantially below said acquisition data rate, each display event displaying one of said measurement data;
   a criterion input unit configured by the user prior to any one of the each acquisition session to designate at least one user designated measurement criteria out of a plurality of available analysis criteria for said measurement data; and
   a processor including the criterion input unit and configured to automatically query which criteria are user designated criteria and process sequential MTIs of the measurement data during said continuous test time period, and choose from each MTI of said measurement data any number of alarmed events with associated measurement data that satisfies said designated criteria, for being displayed on said user display in real time;
   and,
   wherein the measurement and display system is a single-unit device.

2. The system of claim 1, wherein the processor is configured to retrievably store the measurement data that satisfies said measurement criteria for later viewing.

3. The system of claim 1, wherein the processor is configured to produce on said user display one or more of a blinking or a changing or a persistent alarm condition, to signal to a user the acquisition of measurement data that satisfies the measurement criteria.

4. The system of claim 1, wherein the processor is configured to choose said portion of said measurement data that satisfies said measurement criteria on the basis of the satisfaction of at least two of the measurement criteria.

5. The system of claim 1, wherein the processor is configured to store the sensor facility's positions relative to the test object and to associate the positions with corresponding measurement data.

6. The system of claim 2, wherein the stored information includes time, the measurement time intervals, alarm criteria and waveform information.

7. The system of claim 1, wherein the real time information includes one or more of a waveform, a waveform marker, numeric readings and an alarm current indicator.

8. The system of claim 1, wherein the sensor facility comprises an ultrasonic sensor.

9. The system of claim 1, wherein the sensor facility comprises an eddy current sensor.

10. The system of claim 1, wherein the system comprises a microprocessor with memory and embedded program software, a signal processor comprising analog to digital converters, and filters.

11. The system of claim 1, wherein the acquisition data rate is at least four times as high as the display rate.

12. The system of claim 1, wherein the user processor is configured to display only one of several data parameters sensed by the sensor facility, in given, repeating groups of data parameters.

13. The system of claim 1, wherein the user display comprises a waveform display area and an alarm indicator.

14. The system of claim 1, wherein each measurement time interval is associated with a response echo, a gate signal and a predetermined time interval.

15. The system of claim 1, wherein a measurement time interval is expressed as a thickness at which a test object is examined.

16. The system of claim 1, wherein the system further comprises an alarm output and further includes a keypad configured with the criterion input unit.

17. A measurement and display method to display measurement data on a user display of a non-destructive device configured to perform non-destructive inspection, comprising the steps of:
  acquiring measurement data from a test object during a continuous test time period, at an acquisition data rate associated with a plurality or measurement time intervals (MTI) for each acquisition session;
  querying which at least two of the plurality of criteria are user designated criteria for said measurement data;
  processing sequential MTIs of the measurement data during said continuous test time period, and choosing from each MTI of said measurement data any number of alarmed events with associated measurement data that satisfies said designated criteria;
  displaying the alarmed events at a rate lower than the acquisition data rate;
  wherein said displaying steps are concurrent with the acquiring step.

18. The method of claim 17, further including designating measurement criteria selected from one or more of: a) a first echo amplitude; b) a maximum amplitude echo; c) a minimum amplitude echo; d) a minimum time interval; and e) a maximum time interval.

19. The method of claim 17, including setting the acquisition data rate to be at least four times as high as the display rate.

20. The method of claim 17, including displaying a waveform and operating an alarm indicator through a display.

21. The method of claim 17, wherein acquiring data for each of said measurement time interval includes acquiring a response echo and a gate signal.

* * * * *